United States Patent [19]

Bergström et al.

[11] Patent Number: 5,785,522
[45] Date of Patent: Jul. 28, 1998

[54] METHOD OF TREATING SURGICAL DRILL, SURGICAL DRILL AND USE OF SURGICAL DRILL

[75] Inventors: Nils Gustav Bergström, Vagnhärad; Anders Holmén, Billdal, both of Sweden

[73] Assignee: Astra Aktiebolag, Sodertalje, Sweden

[21] Appl. No.: 338,628

[22] Filed: Feb. 7, 1995

[30] Foreign Application Priority Data

May 27, 1992 [SE] Sweden .................. 9201670

[51] Int. Cl.⁶ .................................. A61B 17/56
[52] U.S. Cl. .................. 433/72; 433/165; 433/173; 606/80
[58] Field of Search ............... 606/80, 79, 180, 606/167, 170; 433/25, 72, 102, 103, 114, 125, 142, 144, 165, 166, 173; 408/144, 145, 199, 213, 226

[56] References Cited

U.S. PATENT DOCUMENTS

| | | | |
|---|---|---|---|
| 4,461,799 | 7/1984 | Gavrilov et al. | 428/210 |
| 4,681,541 | 7/1987 | Snaper | 433/165 |
| 4,704,055 | 11/1987 | Guhring | 408/59 |
| 4,708,542 | 11/1987 | Emanuelli | 408/144 |
| 4,897,037 | 1/1990 | Appleby . | |
| 5,125,838 | 6/1992 | Seigneurin . | |
| 5,190,548 | 3/1993 | Davis | 606/80 |

FOREIGN PATENT DOCUMENTS

| | | |
|---|---|---|
| 3339004 | 6/1985 | Germany . |
| 3622676 | 3/1987 | Germany . |
| 588854 | 6/1977 | Switzerland . |
| 614372 | 11/1979 | Switzerland . |
| 2203343 | 10/1988 | United Kingdom . |

*Primary Examiner*—Guy V. Tucker
*Attorney, Agent, or Firm*—White & Case

[57] ABSTRACT

The invention relates to a surgical drill made of metal, for instance made of surgical grade stainless steel or carbon steel, intended for use when implanting cylindrical implants into bone tissue, preferably dental implants made of titanium. The body (3) of the drill (1) is coated by a thin layer of titanium nitride (TiN). The layer of titanium nitride is brightly colored and circumferential bands (8, 9, 10, 11) having a darker color have been etched around the envelope surface of the body (3) of the drill, said bands (8, 9, 10, 11) being located at predetermined distances from each other and having predetermined widths.

9 Claims, 1 Drawing Sheet

METHOD OF TREATING SURGICAL DRILL, SURGICAL DRILL AND USE OF SURGICAL DRILL

This application is filed under 35 USC 371 based on PCT/SE93/00452, filed on May 19, 1993.

TECHNICAL FIELD OF THE INVENTION

The invention relates to surgical drills made of metal, for instance made of surgical grade stainless steel, which are intended for use when implanting cylindrical implants into bone tissue, preferably dental implants made of titanium. The invention also relates to a method for treating such drills and to the use of such drills.

BACKGROUND OF THE INVENTION

When implants are fitted into bone tissue, different kinds of metallic surgical tools are used to prepare the site in the tissue where the implant is to be located. These tools normally are made of carbon steel (normally in disposable tools) or surgical grade stainless steel (normally in non-disposable tools).

In some cases it may however be advantageous if at least the surface of the tools are covered with a material which is more biocompatible than the material in the tool even if the tool is not to remain in the bone tissue for a long period of time. This material of course should be equally hard or harder than the material in the tool. This is particularly advantageous in drills. Drills will be in a close contact with the tissue during a relatively long period of time since their sides are in rotary contact with the sides of the borehole during the entire time the front part of the drill is cutting through the bone tissue. If the drill is not of an inert material as regards the chemical environment prevalent in bone tissue and blood, some slight contaminations may affect the sides of the bore hole. These contaminants can affect the so-called osseointegration process which is important in connection with bone implants and which seems to be sensitive in respect of contaminants.

Another prerequisite for a good osseointegration is a good, stable fit between bone tissue and implants, the osseointegration being dependent on a close contact between bone tissue and implant surface. When a bore-hole for an implant is drilled, it therefore is important that the length of the bore-hole corresponds as closely as possible to the length of the implant chosen.

It is also very important that the bore-holes are drilled to an exact, pre-determined depth in the parts of the jaw where the nerve is located in order to avoid damage to the nerve.

BRIEF DESCRIPTION OF THE INVENTIVE CONCEPT

The above problems are solved in that a drill of the kind described introductorily is coated by a thin, brightly colored layer of titanium nitride (TiN). Titanium nitride has a higher level of biocompatibility than the materials normally used in surgical drills.

In a preferred embodiment circumferential band(s) having a darker color have been etched in the brightly colored layer of titanium nitride around the envelope surface of the drill. Said bands are located at predetermined distances from each other and have predetermined widths.

Further advantageous embodiments and a use of a drill according to the invention are set forth in the dependent claims. A method of obtaining a drill according to the invention is set forth in the independent claim 6.

BRIEF DESCRIPTION OF THE APPENDED DRAWING

FIG. 1 shows a preferred embodiment of a drill according to the invention in a longitudinal side view.

DETAILED DESCRIPTION OF A PREFERRED EMBODIMENT OF THE INVENTION

Figure 1:
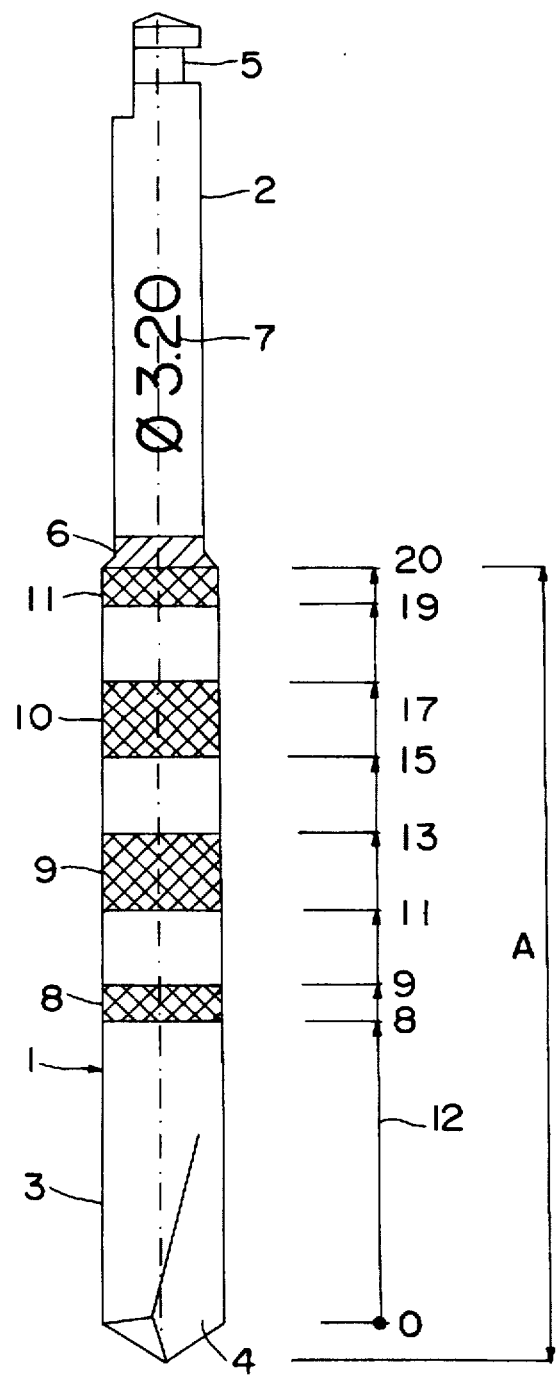

A drill 1 designed in accordance with the invention is shown in the drawing. The drill is provided with a shank designed with a tang 5 designed in accordance with ISO 1797. The diameter of the drill is etched in the shank, at 7. The drill in this particular case is manufactured of stainless steel W.Nr 1.4034, AISI 420.

The drill 1 further is provided with a fluted body 3 having two helical flutes 4, only one being indicated. The neck between the body and the shank is provided with a colored band 6 identifying the size of the drill in that each size of drill has a band of a different color.

The entire length A of the body is covered with a thin layer of titanium nitride having a bright yellow color.

As indicated by means of the chain of measurements 12, a dark band 8 having a width of 1 mm is located at a distance of 8 mm from the tip of the drill 1. Each following dark band 9, 10, 11 is separated from the adjacent band by means of a space having a width of exactly 2 mm. Since the titanium nitride has a bright yellow color and the darker bands are almost black, a very distinct level indication is given at each boundary line between darker bands and lighter areas.

The drill according to the invention can be fabricated in the following steps:

a) coating the drill with a thin layer of titanium nitride (TiN) by means of chemical vapour deposition until the drill obtains a bright permanent color.

b) etching circumferential bands with pre-determined widths being located at pre-determined distances from each other around the outer surface of the drill by means of a laser beam, the bands thus being dark and sharply defined.

The use of a laser beam has the advantage that the boundary lines will be very sharp and well defined and that the contrast between darker and lighter areas will be high.

The etched areas will remain essentially smooth in spite of the treatment, which ensures that there will be no rough areas on the drill upon which contaminants easily will adhere.

When the drill is to be used, for instance in order to implant a screw-shaped fixture for a dental implant, the type of fixture is first chosen in accordance to the prevailing conditions in the jaw, i. e. for instance the shape of the jaw-bone. A drill having a diameter adapted to the diameter of the implant is then chosen and a hole is bored into the jaw-bone. As mentioned above, the drill is provided with dark, circumferential bands corresponding to the lengths of a series of standard sizes of implants having a diameter corresponding to the diameter of the drill. The bore-hole is drilled to a depth determined by that boundary between darker band and lighter titanium nitride surface which corresponds to the implant chosen. The fixture is then screwed into the jaw bone. Since the depth of the hole exactly corresponds to the length of the fixture (or of the threaded part thereof), the fixture will fit closely in the hole.

Bone implants may also be relatively smooth instead of being provided with threads. This kind of implants sometimes are carefully tapped into place in a borehole in the bone by means of a small hammer. The bore-hole may have a diameter which is slightly narrower than the diameter of the implant. However carefully this is done, there always is a risk that the fixture may be pushed to far down into the hole if the length of the hole does not exactly correspond to the fixture. The drill according to the invention thus may be particularly useful in this case, since it may be difficult to extract an implant which has been pushed to far down into a hole.

These problems might also arise if the bore-hole is to shallow for the implant. In both cases the act of extraction per se might cause a trauma to the walls of the bore-hole which might have a deleterious influence on the osseointegration process.

If the surface of the bone into which the fixture is to be inserted is obliquely oriented relative to the longitudinal direction of the hole, the above-mentioned boundarys on the drill will also serve as indexes on a ruler for measuring the difference in level between the edges of the bore-hole and will consequently be very useful when determining how deep the hole has to be in order to house the implant correctly in relation to the oblique surface of the bone.

It should be emphasized that the invention is not limited to the embodiment described above and can be varied in many ways within the scope of the appended claims.

In particular, the invention should not be considered to be limited to the field of dental implants. The invention thus also is applicable to the entire field of implants in bone tissue.

Furthermore, the bore-hole for instance could be bored in two stages a first stage with a narrow pilot drill and a second stage with a full-size drill. It might also be conceivable to provide only one band on the drill body.

We claim:

1. A metallic surgical drill adapted in use to drill a bore into a bone tissue structure for implantation of a cylindrical implant selected from a set of cylindrical implants of different predetermined insertion lengths in the bone tissue structure, the drill having a body with an insertion end which presents a drill tip and an outer surface which is provided with a thin titanium nitride coating on which there is presented a series of spaced apart circumferential bands of contrasting color and predetermined width wherein the boundary lines of the circumferential bands are disposed at different predetermined distances from a predetermined datum point at the insertion end of the body corresponding to the different predetermined insertion lengths of the implants in the set whereby the surgical drill is able to drill a bore of correct depth for any implant selected from the set for implantation in the bone tissue structure by drilling into the bone tissue structure up to the boundary line corresponding to the predetermined insertion length of the selected implant.

2. Surgical drill according to claim 1 wherein the outer surface is provided with a brightly colored layer of titanium nitride on which there is etched circumferential bands having a darker color.

3. Surgical drill according to claim 1 or claim 2 wherein each band has a width of 2 mm. apart from the band located nearest to the drill tip of the drill and the band furthest from the drill tip which have a width of 1 mm, the distance between the boundary lines of adjacent bands being 2 mm.

4. In combination, a cylindrical implant having a predetermined insertion length for insertion into a bore in a bone tissue structure and a metallic surgical drill adapted in use to drill the bore into the bone tissue structure, the drill having a body with an insertion end which presents a drill tip and an outer surface which is provided with a thin titanium nitride coating on which there is presented a circumferential band of contrasting color and predetermined width having a boundary line disposed at a predetermined distance from a predetermined datum point at the insertion end of the body which corresponds to the predetermined insertion length of the implant whereby drilling a bore into the bone tissue structure with the surgical drill up to the boundary line results in the bore having a depth which corresponds to the predetermined insertion length of the implant.

5. In combination, a set of cylindrical implants having different predetermined insertion lengths for insertion into bores in a bone tissue structure and a metallic surgical drill adapted in use to drill a bore into the bone tissue structure, the drill having a body with an insertion end which presents a drill tip and an outer surface which is provided with a thin titanium nitride coating on which there is presented a series of spaced apart circumferential bands of contrasting color and predetermined width wherein the boundary lines of the circumferential bands are disposed at different predetermined distances from a predetermined datum point at the insertion end of the body corresponding to the different predetermined insertion lengths of the implants in the set whereby the surgical drill is able to drill a bore of correct depth for any implant in the set by drilling into the bone tissue structure up to the boundary line corresponding to the predetermined insertion length of the implant selected from the set for implantation in the bone tissue structure.

6. Combination according to claim 4 or 5 wherein the outer surface of the surgical drill is provided with a brightly colored layer of titanium nitride on which there is etched a circumferential band or bands having a darker color.

7. Combination according to claim 4 or 5 wherein each implant is a dental implant.

8. Method for providing the outer surface of the surgical drill of any one of claims 7, 8 or 9 with the thin titanium nitride coating comprising the steps of:

a) coating the outer surface of the drill with a thin layer of titanium nitride (TiN) by means of chemical vapour deposition until the drill obtains a bright permanent color, and then b) etching dark, sharply defined spaced apart circumferential bands of predetermined widths at pre-determined locations on the outer surface of the drill by means of a laser beam.

9. A method of implanting a cylindrical implant into a bone tissue structure comprising the steps of:

a) providing a set of cylindrical implants having predetermined different insertion lengths of corresponding diameter, b) providing a metallic surgical drill adapted in use to drill a bore into the bone tissue structure, the drill having a body of diameter corresponding substantially to that of the insertion lengths of the implants with an insertion end which presents a drill tip and an outer surface which is provided with a thin titanium nitride coating on which there is presented a series of spaced apart circumferential bands of contrasting color and predetermined width, the boundary lines of the circumferential bands being disposed at different predetermined distances from a predetermined datum point at the insertion end of the body corresponding to the different predetermined insertion lengths of the implants, c) selecting an implant from the set with the correct predetermined insertion length for the prevailing conditions in the bone tissue structure, d) drilling a bore into the bone tissue structure with the surgical drill up to the boundary line of the circumferential band corresponding to the predetermined insertion length of the selected implant, and e) inserting the predetermined insertion length of the selected implant into the bore.

* * * * *